United States Patent [19]

Ohtsuka et al.

[11] 4,307,013

[45] Dec. 22, 1981

[54] METHOD FOR REMOVING ANTIGENICITY FROM PEPTIDE

[75] Inventors: Kazumasa Ohtsuka, Yokohama; Michihiko Takahashi, Kashiwa; Masako Araki, Tokyo; Zen Mitsui, Higashikanamachi, all of Japan

[73] Assignee: Nippi, Incorporated, Tokyo, Japan

[21] Appl. No.: 193,117

[22] Filed: Oct. 2, 1980

[51] Int. Cl.$^3$ .................... A23J 1/10; C07G 7/00; C09H 7/00
[52] U.S. Cl. .................... 260/117; 260/112 R; 260/118; 260/123.7; 424/85; 424/177
[58] Field of Search .................... 260/117, 118, 123.7, 260/112 R

[56] References Cited

U.S. PATENT DOCUMENTS

| | | | |
|---|---|---|---|
| 2,669,559 | 2/1954 | Reid | 260/112 R |
| 3,234,199 | 2/1966 | Reid | 260/112 R |
| 4,130,555 | 12/1978 | Ohtsuka et al. | 260/123.7 |

*Primary Examiner*—Howard E. Schain
*Attorney, Agent, or Firm*—Browdy and Neimark

[57] ABSTRACT

A method for removing antigenicity from peptide derived from a collagen-containing material or gelatin by hydrolyzing it with aid of an inorganic acid is disclosed. The method is carried out by passing the peptide through a mixture of a cation-exchange resin and an anion-exchange resin. The thus treated peptide may be further passed through a membrane for ultrafiltration to remove pyrogenous substances completely. The peptide obtained is useful as an additive, diluent or carrier for cosmetic articles or drugs.

5 Claims, No Drawings

METHOD FOR REMOVING ANTIGENICITY FROM PEPTIDE

This invention relates to a method for removing antigenicity from peptide derived from collagen-containing materials or gelatin by hydrolyzing such material or gelatin with aid of an inorganic acid, which comprises treating the hydrolyzate with an ion-exchange resin.

It is known that animal skin, bone, tendon or the like is partially hydrolyzed with aid of an inorganic acid, organic acid, a base, or an enzyme and the resulting oligopeptide is utilized as a surfactant for various cosmetic articles and detergents. The hydrolizate such as peptide derived from natural sources is advantageously used, especially, in the field of cosmetic articles, because such natural source-derived pepride causes less irritation when directly contacted with human skin.

In addition to such properties, the natural source-derived peptide is useful as a nutritious additive for protein-enriched beverage and food. In particular, when the peptide is added to an acidic beverage such as juice, it does not cloud nor substantially reduce its initial refreshness. Also, such peptide is useful as a food modifier, especially, as a foaming agent for food.

On the other hand, the use of gelatin as a plasma expander such as clinical dextran (molecular weight: about 70,000), low molecular dextran (molecular weight: about 40,000), hydroxyethylstarch (HES) or the like has often been tried. However, it has not been satisfactory because gelatin has undesired antigenicity and undesired gellatin property and is easily contaminated with bacteria.

The use of a peptide derived from a collagen-containing material or gelatin has been tried for the same purpose. However, it also has an undesired antigenicity.

An object of this invention is to provide a method for reducing antigenicity of the peptide to provide a peptide for clinical use having no or very low antigenicity.

Collagen-containing material which can be used in this invention includes any material containing collagen, and advantageously, materials which are usually considered as waste materials such as animal skin, bone, tendon or the like tissue because of their low cost.

Gelatin which is useful as a raw material in this invention includes any commercial grade of gelatin such as industrial or food grade of gelatin.

A method of this invention is carried out as follows.

A collagen-containing material or gelatin is used as a raw material as it is or after cutting it into small chips. The material is soaked or dispersed in water. The amount of water is not critical, but usually 2-3 times as much as the volume of the raw material is used. An inorganic acid such as hydrochloric acid or sulfuric acid is added to water containing the raw material. The mixture is heated to dissolve the material in water.

The desired hydrolyzing degree can be achieved, for example, by heating the mixture at 70° to 80° C. for 3-5 hours in water containing hydrochloric acid at a concentration of 0.3 to 2.0%.

The resulting solution is passed through a column filled with a mixture of a cation-exchange resin and an anion-exchange resin to give an aqueous peptide solution having no or very low antigenicity.

The cation-exchange resin which can be used in this invention includes any sulfonic type of ion-exchange resin, for example, those sold under the name of Dowex 50 W, Amberlite IR-120B or the like.

The anionic-exchange resin which is useful in this invention includes any quaternary ammonium type of resin, such as those commercially available under the trade name of Dowex 1, Dowex 2, Dowex 21K, Amberlite IRA-400 or the like.

Substances having high antigenicity which are removed according to this invention have not been exactly identified, but they have a relatively low molecular weight and are relatively rich in lysine and arginine. According to the method of this invention, such substances with high antigenicity are believed to be absorbed on a mixed bed of ion-exchange resins and removed from the hydrolyzate.

The peptide having essentially no antigenicity obtained according to the method of this invention is relatively rich in proline and hydroxyproline which are the main components of the crystalline parts of collagen, and contains less lysine or arginine which is rich in the amorphous part of the original collagen.

If desired, the peptide with no or low antigenicity may be subjected to ultrafiltration to completely remove pyrogenous substances. The ultrafiltration can be carried out by using a membrane through which the peptide solution obtained according to the method of this invention is passed. The membrane which can be used includes any type of commercially available membranes for ultrafiltration, such as those made of cellulose acetate, polyacrylonitrile, polyamide, polysulfone and the like. Examples of commercially available membranes are those sold under the name of UF Module from Romicon Inc., and under the name of UM series, PM series, DM series and XM series of products from Amicon Far East Ltd. The hollow tube type of membrane is convenient and effective in the practice of this invention.

The pore size of the membrane depends on the desired molecular weight of the peptide, but is usually between 10,000 and 100,000 in terms of fractionating molecular weight; in other words this is the upper limit and peptide having a higher molecular weight is not passed through the membrane. If a peptide having a molecular weight of more than 10,000 is desired, the membrane used should have a pore size corresponding to frantionating molecular weight of from 50,000 to 100,000 or more.

The peptide, the antigenicity of which is removed, can be used as a plasma expander or as a diluent or stabilizer for parenteral solution for intravenous administration.

The desired molecular weight of the peptide can vary within the range of from 600 to 50,000 depend on the particular utility.

This invention is further illustrated by the following Example and Experiment.

EXAMPLE (a) Gelatin (12 g) which was derived from cattle bones was dissolved in water (40 ml), and 35% chloric acid (1 g) was added to the solution. The solution was heated at 70° to 80° C. for 3 hours to hydrolyze the gelatin. The treated solution was passed through a colum filled with a mixture of a cation-exchange resin (20 ml) sold under the name of Amberlite IR-120B (H-form) and an anion-exchange resin (40 ml) sold under the name of Amberlite IRA-400 (OH-form). The passed solution contained peptide having a molecular weight of about 10,000.

(b) After recovering the peptide solution, the fraction absorbed on the resins was eluted with 1 N hydrochloric acid and the eluate was passed through a resin sold under the name of Amberlite IR-45 to remove hydrochloric acid to give an eluate sample solution.

EXPERIMENT: CONFIRMATION OF ANTIGENICITY

(a) Method of Immunization

The peptide and eluate solutions obtained in Example (a) and (b), were dissolved in respective physiological saline solutions buffered with phosphoric acid to give solutions containing 5 mg of the test solution per ml of the resulting solution. Each of the resulting solutions was emulsified with an equal volume of Freund complete adjuvant.

Two rabbits and two guinea pigs were used as test animals for each sample solution. The rabbit was sensitized by subcutaneously injecting the sample above in the back at four separate places in a dose of 0.5 ml of the sample per injection (total amount: 2 ml per rabit). In a similar manner, a guinea pig was sensitized with the same sample at two places on its back by injection in a dose of 0.5 ml (1 ml of total doses).

The sensitization was repeated every week for 3 weeks for each animal, and 3 days after the last sensitization, the blood was sampled and the formation of an antibody against the test sample solution was confirmed.

(b) Method of Confirmation of Antibody

Serum recovered from the sampled blood was diluted to 5, 10, 20, or 40-fold in volume with a physiological saline. Each of the diluted solutions (0.1 ml) was subcutaneously injected in the back of a guinea pig and 5 hours after the injection, the guinea pig was intravenously injected with 1 ml of 1% Evans Blue containing 2 mg of the antigen which was the same as that used in the initial sensitization.

Fifteen to thirty minutes after the injection, the guinea pig was sacrificed by etherization and stripped of the skin, and the dye which had leaked from the site of serum injection into the inside of skin was observed by the naked eye. (passive local anaphylaxis test-PCA reaction)

(c) Test Results

With respect to one of the two rabbits immunized by the eluate solution, positive reaction was observed when using 5-fold diluted solution. In contrast, in both rabbits and guinea pigs no formation was observed at any dilution level.

What is claimed is:

1. A method for removing antigenicity from peptide derived from collagen-containing materials or gelatin by hydrolyzing the material or gelatin with aid of an inorganic acid, which comprises passing the peptide through a mixture of a cation-exchange resin and anion-exchange resin.

2. A method according to claim 1 wherein said cation-exchange resin is a sulfonic type of ion-exchange resin and said anion-exchange resin is an ammonium type of ion-exchange resin.

3. A method according to claim 1 wherein said hydrolysis is carried out under such conditions that the molecular weight of the peptide is between 600 and 50,000.

4. A method according to claim 3 wherein said hydrolysis is carried out in water containing hydrochloric acid at a concentration of from 0.3 to 2.0% at 70° to 80° C. for 3 to 5 hours.

5. A method according to any one of claims 1 to 4 wherein the peptide passed through the mixture of ion-exchange resins is further subjected to ultrafiltration to remove pyrogenous substances.

* * * * *